United States Patent [19]

Matsuo et al.

[11] Patent Number: 5,376,548
[45] Date of Patent: Dec. 27, 1994

[54] BIOREACTOR APPARATUS

[75] Inventors: Shigeru Matsuo, Tokyo; Masato Nishimura, Osaka, both of Japan

[73] Assignees: Fuji Photo Film Co., Ltd., Kanagawa; Kirin Brewery Co., Ltd., Tokohama, both of Japan

[21] Appl. No.: 75,335

[22] Filed: Jun. 11, 1993

Related U.S. Application Data

[63] Continuation of Ser. No. 720,048, Jun. 24, 1991, abandoned.

[30] Foreign Application Priority Data

Jun. 29, 1990 [JP] Japan .................................. 2-172178

[51] Int. Cl.$^5$ .......................... C12M 3/00; C12M 3/06; C12M 3/04
[52] U.S. Cl. .................................... 435/284; 435/285; 435/311
[58] Field of Search .................... 435/240.23, 240.241, 435/240.243, 283–286, 288, 296, 299, 310, 311, 313, 315, 316, 813

[56] References Cited

U.S. PATENT DOCUMENTS

| | | | |
|---|---|---|---|
| 3,853,712 | 12/1974 | House et al. | 435/285 |
| 4,546,083 | 10/1985 | Meyers et al. | 435/284 |
| 4,833,083 | 5/1989 | Saxena | 435/284 |
| 4,861,725 | 8/1989 | Liau | 435/311 |
| 5,057,428 | 10/1991 | Mizutani et al. | 435/284 |

FOREIGN PATENT DOCUMENTS

| | | |
|---|---|---|
| 56-42584 | 4/1981 | Japan . |
| 59-59187 | 4/1984 | Japan . |
| 6434276 | 2/1989 | Japan . |

Primary Examiner—William H. Beisner
Attorney, Agent, or Firm—Sughrue, Mion, Zinn, Macpeak & Seas

[57] ABSTRACT

A bioreactor apparatus for producing metabolites from bioorganisms by depositing the animal cells on a carrier made of a porous material. The apparatus includes a hermetically sealed container (1) having a first supply channel A, for supplying a liquid containing animal cells into the inside thereof, a second supply channel (B) for supplying a culture solution and a substrate solution into the inside thereof, a first exhaust channel (a) for exhausting a liquid containing suspended animal cells from the inside thereof, and a second exhaust channel (b) for exhausting a residual part of the culture solution, a residual part of the substrate solution and a solution containing metabolites of the animal cells from the inside thereof. Disposed within the container is an animal culture base including a porous carrier (31, 33, 34) and a culture bed (4) arranged so that liquid supplied from the supply channels (A, B) are brought into contact therewith while flowing in the inside of the container (1). Further, the apparatus includes a filtration membrane (6) arranged across the second exhaust channel (b) in the inside of the container (1) and provided for filtrating a liquid to be exhausted through the second exhaust channel (b).

7 Claims, 2 Drawing Sheets

BIOREACTOR APPARATUS

This is a continuation of application Ser. No. 07/720,048 filed Jun. 24, 1991, now abandoned.

BACKGROUND OF THE INVENTION

The present invention relates to a bioreactor apparatus, and particularly relates to a bioreactor apparatus for producing metabolites such as human body cure vaccines, interferons, cancer antigens, hormones, cell growth factors, lymphocines, various kinds of catalysts, and the like, from bioorganisms such as various kinds of animal cells and the like through depositing the animal cells on a carrier made of a porous material such as nonwoven fabric or the like, and cultivating the animal cells with a high yield and density on the carrier, by which various useful physiologically active substances can be produced selectively, continuously and efficiently.

For in-vitro production of useful substances produced by various human cells, such as human immuno chemical mediators, human type enzymes, etc., for medicinal application it, is necessary to establish both a technique for mass-cultivating various kinds of animal cells and develop a high-performance bioreactor apparatus.

The animal cell cultivating techniques used heretofore include "a suspension growth technique" for growing cells suspended in an aqueous solution, "a microcarrier growth technique" for growing suspended cells by adhering the cells with porous microbeads having a diameter of about 200 μm, "an adhesion carrier growth technique" for growing cells by carrying the cells on an adequate nonporous and/or porous carrier (such as porous film, hollow fiber, nonwoven fabrics etc), and the like.

Japanese Patent Unexamined Publication No. Sho. 59-59187 discloses a cultivating apparatus for performing the adhesion carrier growth technique in which animal cells are adhered or grown on various forms of culture supports housed in a culture container of the apparatus while a culture solution is sprayed and supplied into the container.

Japanese Patent Unexamined Publication No. Sho. 56-42584 discloses a cultivating apparatus designed to pack hollow fibers in a culture container fill space between a wall of the container and an outer surface of the hollow fiber with suspended cells and supply a culture solution from the inside of the hollow fiber. Further, Japanese Patent Unexamined Publication No. Sho. 64-34276 discloses a material for performing the adhesion carrier growth technique, in which nonwoven fabric made from specific superfine fiber is used as a carrier for a cell culture bed and is arranged in a plastic schale (laboratory dish) to cultivate animal cells.

However, in the conventional suspension growth technique and the microcarrier growth technique, the concentration of floated or suspended animal cells is limited to a maximum of about 10 g/l. Further, the concentration of the substrate solution cannot be increased because of substrate inhibition and osmotic pressure. Furthermore, shear forces imposed on cells in the solution by contact, collision, abrasion, etc., of the cells with the fluidal change of solvent are so large that the cells are often inactivated or killed. In the microcarrier growth technique, the cells are, in most cases, separated or dropped from the microbeads. In the adhesion carrier growth technique, it is not only difficult to continuously circulate and exchange the culture solution and the substrate solution and to supply the necessary oxygen for cultivating animal cells, but the contact of the cells with the culture solution and the substrate solution is uneven, insufficient and inefficient. Furthermore, metabolites cannot be continuously separated to the outside of the apparatus. As a result, nutritional balance disorder caused by excess or shortage of the substrate and culture environment disorder caused by storage of the metabolites occur locally in the cells. Consequently, animal cells cannot be cultivated in a high yield and a high density per volume. Further, efficient metabolite production is impossible. Among the conventional apparatuses for performing the aforementioned techniques, there is no apparatus for solving these problems.

SUMMARY OF THE INVENTION

The present inventors have made intense studies to solve the aforementioned problems in the prior art in order to arrive at the present invention. Accordingly, the present invention is directed to a bioreactor apparatus comprising: a hermetically sealed container having a supply channel A for supplying a liquid containing animal cells into the inside thereof, a supply channel B for supplying a culture solution and a substrate solution into the inside thereof, an exhaust channel a for exhausting a liquid containing suspended animal cells from the inside thereof, and an exhaust channel b for exhausting a residual part of the culture solution, a residual part of the substrate solution and a solution containing metabolites of the animal cells from the inside thereof; an animal cell culture base composed of a porous carrier and a culture bed provided on the carrier and arranged so that liquids supplied from the supply channels are brought into contact with each other while flowing in the inside of the container and then led to the exhaust channels; and a microfiltration membrane arranged across the exhaust channel b in the inside of the container for filtrating a liquid to be exhausted to the exhaust channel b. In particular, the porous carrier is made of nonwoven fabric. Further, the animal cell culture base is arranged so as to be entirely penetrated by the substrate solution supplied into the container. In the case where the base is shaped like a film, the base is arranged. spirally or arranged in the form of a laminate composed of a large number of sheets. In particular, the animal cell culture base is adapted for adhesion and fixation of animal cells to be cultivated. The liquid supplied into the container contains nutriments necessary for cultivating animal cells or contains a substrate for acting on cultivated animal cells to produce a predetermined metabolite. The liquid supplied into the container contains oxygen in a necessary and sufficient amount for the dual purpose of cultivating animal cells and maintaining activity thereof. In particular, the liquid exhausted from the container contains at least one substance produced by cultivated animal cells.

DETAILED DESCRIPTION OF THE INVENTION

Figure 1:
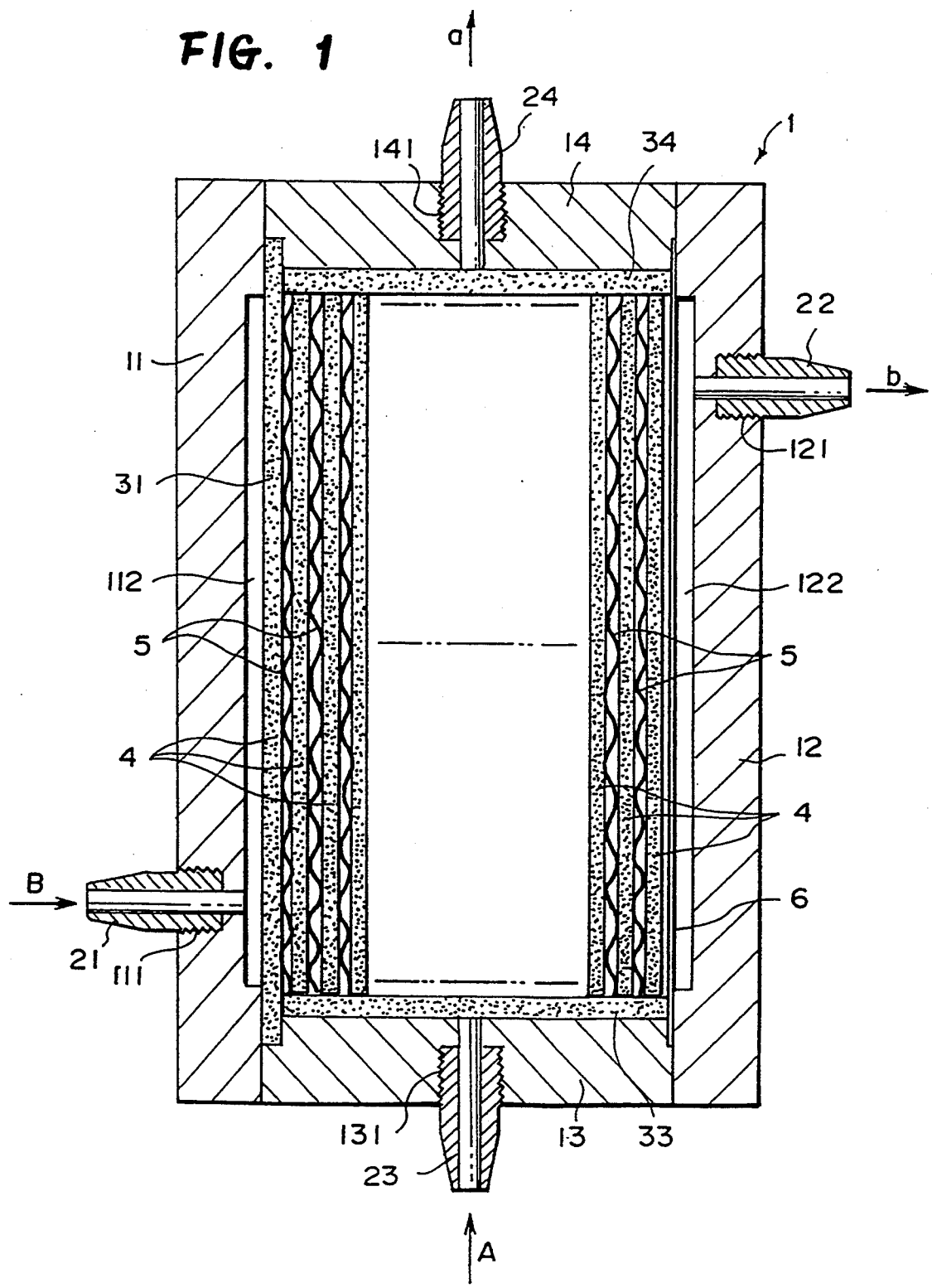
FIG. 1 is a sectional view of a bioreactor apparatus filled with laminate-type culture film as an embodiment of the present invention.

The present invention will be described below in detail.

The hermetically sealed container used in the present invention is a shell member of a bioreactor apparatus and a container for cultivated animal cells to produce a target useful substance from the cultivated animal cells. Examples of preferred materials for the container are stainless steel, ceramics such as ceramics, hard glass, etc., heat-resisting polymer capable of being treated with hot steam such as polycarbonate, polysulfone, polyethersulfone, polyetheretherketone, etc., and the like. In particular, in the case where observation of the inside of the container is required, it is preferable that the container is made of a transparent material. The inside structure of the container varies according to the film strength or the arrangement form of the material used for the animal cell culture base which will be described later. The container is a member partitioned into two parts in order to incorporate necessary members in the inside thereof. After the necessary inner members (which will be described later) are arranged, all portions except the channels are entirely sealed to prevent liquid leakage. The container has a supply channel A for supplying a liquid containing animal cells into the inside thereof, a supply channel B for supplying a culture solution containing nutriments for cultivating animal cells and a substrate solution into the inside thereof, an exhaust channel a for exhausting a liquid containing suspended animal cells from the inside thereof, and an exhaust channel b for exhausting a liquid containing the culture solution and a solution containing a residual part of the substrate and the metabolite of animal cells from the inside thereof. As described above, the container has a series of channels for supplying and exhausting animal cells and a series of channels for supplying and exhausting both a culture solution and a substrate solution. To supply a liquid into the container without producing bubbles in the liquid, as will be described later, the supply channel in each channel series is generally arranged in a relatively lower portion of the container, whereas the exhaust channel is arranged in the upper portion. Each channel may be composed of a hole penetrating the container wall, and a connection pipe attached thereto. Each connection pipe may be formed of a cylindrical material, a tubular material or the like selected from stainless steel, ceramics such as hard glass, etc., heat-resistant polymer such as polycarbonate, polysulfone, polyethersulfone, polyetheretherketone, etc. and the like. For example, the connection pipes are respectively connected by means of screws, bolts, or the like, with various kinds of packings interposed therein to prevent liquid leakage in the container wall. Of course, the connection pipes may be formed with the container as a single unit. Opposite ends of the supply channels are connected to reservoirs for reserving the necessary liquids.

The animal cell culture base, including a porous carrier and a culture bed applied onto the carrier, is arranged in the inside of the container so that the liquids supplied from the respective supply channels are led to the respective exhaust channels after the liquids flow and come in contact therewith. The porous carrier is a structural material for forming the culture bed in a predetermined shape. In respect to the basic performance of the porous carrier, it is necessary that the porous carrier be inactive with respect to the culture solution and that the substrate solution supplied into the container exhibit a necessary self-supporting property when immersed in the culture solution and be suitable for application of the culture bed (as will be described later). Because the carrier has many pores, it has a very large surface. Further, since there are few dead-end pores, a very large number of animal cells with a high density can be grown on the surface of the carrier. Accordingly, animal cells can be mass-cultivated simultaneously, so that the amount of a useful substance produced by the animal cells in a unit area of the culture base and in a unit time can be improved greatly.

In the case where the carrier is shaped like a film, the carrier is sufficiently flexible that it can be bent or wound to conform to the shape of the container so that it can be placed in the container. Examples of preferred materials for the porous carrier are membrane-like fine porous film, nonwoven fabric, felt, sponge sheet, and the like. Further, the porous carrier is selected from a porous structure in which honeycomb-shaped fine vent pores are formed by a porous material, reticular matters are piled up, different-form porous rod-like or linear matters are used, spherical or different-form porous bead-like or porous pellet-like matters are used as fillers, porous tubular matters are used as fillers, and porous tubular matters are used in combination, and the like. The most preferred materials are various kinds of nonwoven fabric. In any case, the nonwoven fabric has a large specific surface area and has a porous structure constituted by a large number of fine pores. Examples of fiber materials for the nonwoven fabric as the preferred carrier are polyester fiber, nylon fiber, and polyurethane fiber. The preferred material is a fiber material having a fiber packing density of about 10 $g/m^2$ to about 180 $g/m^2$. From the point of view of efficiency in placing the culture bed in the container, the inside, supply and diffusion of a culture medium and nutriments for cultivating animal cells in the inside of the nonwoven fabric, and the like, it is preferable that the thickness of the nonwoven fabric be not larger than 5 mm.

The culture bed is applied to the porous carrier. It is preferable that the culture bed have a high affinity and a high adhesiveness to the animal cells and be suitable for adhesion of the animal cells to the culture bed and for cultivating the animal cells with a high yield and a high density. The preferred materials for the culture bed are various kinds of natural or synthetic hydrophilic high-molecular matters having both an affinity and an adhesiveness to animal cells. The more preferred are aterrocollagen, poly-vinyl alcohol having a photo cross-linking radical, polypeptide, and the like. For application of the culture bed onto the porous carrier by using these materials, the carrier is immersed in an aqueous solution of a matter to form the culture bed, dried by squeezing out excess aqueous solution and then subjected to an insol-forming treatment. For example, aterrocollagen is made insoluble as follows. Aterrocollagen is applied in the form of an aqueous solution having an adequate aterrocollagen concentration and then treated with ammonia and phosphate buffer to be gelated. After being gelated, aterrocollagen is air-dried and then reacted by using ultraviolet radiation, glutaraldehyde, hexamethylene disocyanate, sodium borohydride, epoxy-group cross-linking agent, or the like to introduce a cross-linking structure to aterrocollagen to thereby make it insoluble. For example, poly-vinyl alcohol having a stilbazolium group as a photo cross-linking radical is made insoluble as follows. Poly-vinyl alcohol is applied onto nonwoven fabric by using an aqueous solution containing 1–10% by weight of poly-vinyl alcohol and dried at a temperature of 70° C. Then, ultraviolet rays are radiated to the poly-vinyl alcohol for an adequate time to introduce a cross-linking structure to the poly-vinyl alcohol to thereby make it insoluble. In particular, the cross-linked poly-vinyl alcohol culture medium has a positive (+) surface potential, so that it has a high electrostatic affinity to animal cells having, a negative (−) potential. Further, the culture medium does not inhibit the physical function of animal cells. Accordingly, the medium is excellent for adhesion of animal cells. In any case, the medium has an excellent characteristic in that it can be used in the form of an aqueous solution for application thereof. The matter applied to form the culture bed can be used if it has a molecular weight suitable for forming a coating film. In most cases, the molecular weight of the applied matter is from $10^5$ to $10^6$. The thickness of the culture bed is generally from about 10 to about 1000 $\mu$m.

The animal cell culture base thus prepared is arranged so that the liquids supplied from the respective supply channels can be led to the respective exhaust channels after the liquids come in contact therewith while flowing in the inside of the container. Here, it is important to arrange the culture base so that the supplied liquids can flow efficiently and effectively. In respect to the detailed form of the arrangement, the culture base may be arranged so as to be penetrated by the liquids supplied into the container or may be arranged so that the supplied liquids can flow along the culture film. In the case where the animal cell culture base is shaped like a film, the culture base may be arranged horizontally or may be arranged vertically. In the case where the culture film is arrange horizontally, animal cells can be continuously cultivated without dropping, even if the animal cells are imperfectly adhered in the culture film or are separated from the culture film. Accordingly, in this case, animal cells with a high density can be settled on the culture film.

Further, the supply channel A can be divided into groups so that different liquids can flow to be respectively supplied to spaces between culture films in the container. Further, the animal cell culture film may be arranged spirally in the container or in the form of a laminate prepared by laminating a large number of sheets or by folding a sheet. In the case where the animal cell culture film is arranged in the form of a laminate or a spiral, supply channels for supplying animal cells and the culture solution into the container are formed by arranging separators between respective culture films and arranged the laminated culture films at intervals of a short distance. To form gaps suitable for the dual purpose of supply of animal cells and adhesion thereof to the culture base, it is preferable that the thickness of each separator is from about 0.2 to about 2 mm. As a result, the fluidity and diffusion of the liquid containing animal cells supplied from the supply channel A can be quick and uniform, so that the animal cells can be distributed and uniformly to the entire surface of the culture bed. Furthermore, there is another effect in that the culture solution penetrating the culture films can be further diffused and mixed in the gaps formed by the presence of the separators to thereby attain uniformity of components. The respective separator may be formed of a material having rough gaps or pores. Examples of the preferred form are the form of a porous film or net having a rough pore diameter.

As will be described later by way of example, a rough porous supporting plate may be used for supporting the opposite ends of the culture base and the separator. The supporting plate functions to support the opposite ends of the culture base and the separator and to supply the animal cells from the entire surface of the supporting plate to the container. Accordingly, it is necessary that the supporting plate have continuous through pores with a pore diameter of about 50 to 200 $\mu$m to avoid abrasion of the supplied animal cells caused by the flowing thereof. The preferred material for the porous supporting plate is a hard material or a relatively highly elastic material.

As will be described later, a microfiltration membrane is arranged across the exhaust channel b. Examples of the form of the microfiltration membrane are a flat film, a pleat, a tube, a hollow fiber, a fine porous tube, and the like. The microfiltration membrane prevents the animal cells and the medium suspended from the first or suspended by dropping out of the culture base after adsorbing thereto from flowing out of the container and, at the same time, filtrates a useful substrate produced by the animal cells, to thereby continuously exhaust it to the outside of the container. Since the pressure of the exhausted liquid acts on the microfiltration membrane 6 arranged across the exhaust channel b as described above, sufficient consideration must be given on the settlement of the microfiltration membrane to prevent the membrane from being dislodged in the liquid-feeding operation. As will be described later in the first embodiment, the microfiltration membrane 6 is secured between side walls 12 and then the upper and lower members 13, 14 as illustrated in FIG. 9. At the same time, the microfiltration membrane 6 is placed into the container 1 by compressing or by forcedly inserting the membrane in a frame.

The microfiltration membrane is made of a material having a durability against vapor sterilizing treatment. Examples of the materials for the microfiltration membrane are porous films such as a flat film, a pleat film, a tubular film, a hollow fiber film, a fine tubular film, etc., having a pore diameter of about 1 $\mu$m to the order of tens of microns and being selected from polysulfone, polyethersulfone, poly (vinylidene fluoride), nylon, etc. It is preferable that the material doesn't adhere protein, doesn't occur fouling and doesn't become blocked. Examples of available materials for the microfiltration membrane are "PSE-20", "PSE-45", "PSE-80", "PSE-200" (all tradenames produced by Fuji Photo Film Co., Ltd.), etc. These available materials can be used in the apparatus of the present invention.

In the case where the animal cell culture base is shaped like a film and arranged in the form of a spiral as described above, the container can be provided in the form of a cylindrical container capable of being rotated to provide an apparatus improved in fluidity, diffusion and uniformity of various kinds of liquids supplied into the container.

By using the bioreactor apparatus according to the present invention as constructed above, animal cells are cultivated as follows. The inside of the container is subjected to a sterilizing or germicidal treatment by heating the container or by introducing high-temperature vapor, hot water, aqueous alcohol having an adequate concentration or germicide gas such as ethylene oxide gas, etc. into the container so as to be circulated, if necessary, and then radiated with radiating rays such as ultraviolet rays, λ-rays, etc. In the case where the container or the medium of the treatment is heated in this treatment, it is heated at a temperature of about 120 to about 130° C. for a period of about 5 to about 30 minutes.

After the container sterilizing treatment is finished, the supply pipe of the supply channel A is connected to a tank reserving the liquid containing animal cells whereas the exhaust pipe of the exhaust channel a is connected to a reservoir or is connected to the aforementioned tank if the liquid is circulated. The supply pipe of the supply channel B is connected to a tank reversing the culture solution and the substrate solution whereas the exhaust pipe of the exhaust channel b is connected to an exhaust liquid reservoir.

Then, a liquid containing animal cells is supplied from the supply channel A. The container is filled with the supplied liquid, so that the liquid penetrates the animal cell culture base arranged in the inside of the container. As a result, animal cells are adhered in the culture bed of the culture base. To improve the density of animal cells adhered to the culture bed, the liquid may be introduced into the container again from the supply channel A so as to be circulated between the container and the tank.

The kind of animal cells used in the apparatus of the invention is not limited specifically. Examples of the animal cells are T cell, B cell, killer cell, human tumor cell, fibroblast cell, lymphoblast cell, EB virus mutant cell, etc. These components are respectively mixed and diffused to a concentration ranging approximately from 1 to 100 mg/l (animal cells) with respect to a solvent, such as water. Various kinds of amino acids, vitamins and various kinds of saccharides as another culture medium may be added to the liquid containing animal cells.

Immediately after the supply of animal cells to the culture base is finished, an animal cell culture solution and a substrate solution are supplied from the supply pipe of the supply channel B. These culture and substrate solutions are diffused or fluidized into the container and brought into contact with animal cells on the culture base to thereby contribute to the growth or culture thereof.

The culture solution contains, as main components, nutriments necessary for the growth of animal cells. Examples of the nutriments are various kinds of essential amino acids, various kinds of vitamins, saccharides such as glucose, serum components, etc. These nutriments are provided in the form of an aqueous solution having a concentration of about 1 to about 100 g/l. Because the substrate serves as a raw material for producing a necessary metabolite, a specific metabolite can be selectively produced by specifying the kind of the animal cells and substrate. Examples of the substrate are essential amino acids, various kinds of vitamins, saccharides such as glucose, serum components, etc. The components of the culture solution may be physically equal to those of the substrate but the former is different from the latter in that the former is supplied at the time of cultivating animal cells and for the purpose of cultivating animal cells at the time of cultivating, whereas the latter is supplied for the cultivated or grown animal cells to produce metabolites thereof. The substrate solution is prepared in the form of an aqueous solution having a concentration of about 1 to about 100 g/l, with respect to the aforementioned components.

The supply flow rate in each of the liquid containing animal cells, the culture solution and the substrate solution ranges from about 1 to about 100 ml per minute. The supply flow rate is suitably adjusted according to the adhesive ability of animal cells to the culture bed, the growth rate thereof, the degree of the growth thereof, and the like. These liquids can be recycled between the container and the tank if they can be repeatedly used with no trouble.

For the growth of animal cells, it is preferable that dissolved oxygen be contained in the supplied liquid. It is most preferable that oxygen be saturated. The saturated oxygen concentration is generally about 10 mg/l. Such dissolved oxygen may be contained in any liquid supplied into the container. Further, each of the liquids may contain other necessary components.

The culture solution is continuously supplied to animal cells adhered in the culture bed while factors such as osmotic pressure, dissolved oxygen volume, pH, liquid temperature, substrate concentration of the substrate solution, metabolite concentration, etc. are continuously controlled to an optimum range suitable for cultivating animal cells, by which animal cells can be cultivated with a high yield and a high density.

The animal cells cultivated by the aforementioned operation produce a metabolite by reaction with the substrate. The metabolite is exhausted from the exhaust channel b through the microfiltration membrane, as described above, and collected. Then, the metabolite is extracted from the exhaust liquid and purified to a useful substance. The metabolite varies according to the kind of the animal cells and the substrate given thereto. Examples of the metabolite are cure vaccines, interferons, monoclonal antibodies, cancer antigens, hormones, cell growth factors, lymphocines, various kinds of catalysts and the like.

The present invention will be described more in detail as to the preferred embodiments illustrated in the drawings in which like numerals represent like parts. FIG. 1 is a sectional view showing the schematic configuration of a bioreactor using a stratified animal cell culture film as an embodiment of the present invention. In the drawing, container 1 is composed of side walls 11 and 12, a lower wall 13, and an upper wall 14 (and front and back walls, not shown). The container 1 is formed by combination of the respective walls as illustrated in the drawings. Liquid channels composed of through holes 111, 121, 131 and 141 for penetrating the walls and connection pipes 21, 22, 23 and 24 are formed at predetermined positions of the respective walls, respectively. In this embodiment, the reference numeral 23 designates a supply channel A for supplying a liquid containing animal cells into the container 1, 24 an exhaust channel a for exhausting the liquid supplied from the channel 23 to discharge it or recycle it to the apparatus, 21 a supply channel B for supplying a liquid containing a culture solution containing nutriments to be given to animal cells supported in the container and 22 an exhaust channel b for exhausting the liquid supplied from the supply channel 21 out of the container 1 to discharge it or recycle it from the channel 22 to the apparatus and for exhausting a liquid containing a metabolite produced by the animal cells out of the container 1 to collect the metabolite.

Cavities 112 and 122 are respectively provided in the inside of the wall members 11 and 12 of the container 11. The cavity 112 serves as a liquid reservoir for the liquid supplied from the channel 21 to increase the flow rate of the liquid in the supply channel B. The cavity 122 serves as a liquid reservoir for the liquid exhausted from the channel 22 to lead the flow of the liquid to the exhaust channel b. Accordingly, the cavities can increase the liquid flow efficiency of the respective liquids. In the apparatus as shown in the drawing, the shell of the container 1 is formed by connecting the lower and upper walls 13 and 14 to the upper and lower portions of the side walls 11 and 12 (and the front and back walls) by means of riveting or screwing. In the inside of the container, a rough porous supporting plate 33 contacts the inner surface of the lower wall 13, a rough porous supporting plate 34 contacts the inner surface of the upper wall 14 and a rough porous supporting plate 31 contacts the inner surface of the side wall 11.

As described above, animal cell culture films 4 and sheet-like separators 5 are successively alternately laminated and packed in a space surrounded by the rough porous plates 31, 33 and 34. A microfiltration membrane 6 is arranged between the outermost layer of the laminate and the wall member 12 of the container. Because a considerably large amount of pressure caused by the small size of the pore diameter and the blocking of the pores in the cultivating period acts on the microfiltration membrane 6, it is necessary to compress the microfiltration membrane 6 between the container wall members 12 and 13 and between the wall members 12 and 14, as shown in the drawing.

After the members are arranged in the container as described above and the container wall members are combined with each other, a sterilizing treatment is applied by passing high-temperature vapor from the supply channel A to the exhaust channel b and from the supply channel B to the exhaust channel a for about 30 minutes. Then, an aqueous solution containing about 1 g/l of specific animal cells is supplied from the supply channel A to the container 1 to produce a predetermined metabolite. The cell-containing solution enters into the container, reaches the rough porous plate 34 so as to be diffused to the entire surface thereof, propagates between the separators 5 in the container 1 to fill the container and at the same time penetrates the pore tissues of the culture films 4. The animal cells in the aqueous solution sink onto the tissue surface of the culture films and are then adhered thereto. With the supply of the cell-containing solution, the amount of the adhered cells is increased. The time required for the adhesion of a sufficient amount of the animal cells is from about 30 to about 60 minutes.

After the adhesion of the sufficient amount of the animal cells is confirmed, the supply of the animal cell culture solution from the supply channel B is started. The flow rate of the supplied culture solution is about 10 liters per day.

With the supply of the culture solution to the container 1, the animal cell-containing solution in the container 1 is gradually replaced by the culture solution. The entire replacement is finished about 30 minutes after the starting of the supply. Then, the supply of the culture solution is continued for about 24 hours, so that the animal cells in the container 1 are uniformly grown. As a result, animal cells can be cultivated to a high yield and a high density in the bioreactor apparatus of the invention. Therefore, a predetermined substrate is supplied for a period of one day to 3 days to produce a predetermined yield of the metabolite.

Figure 2:
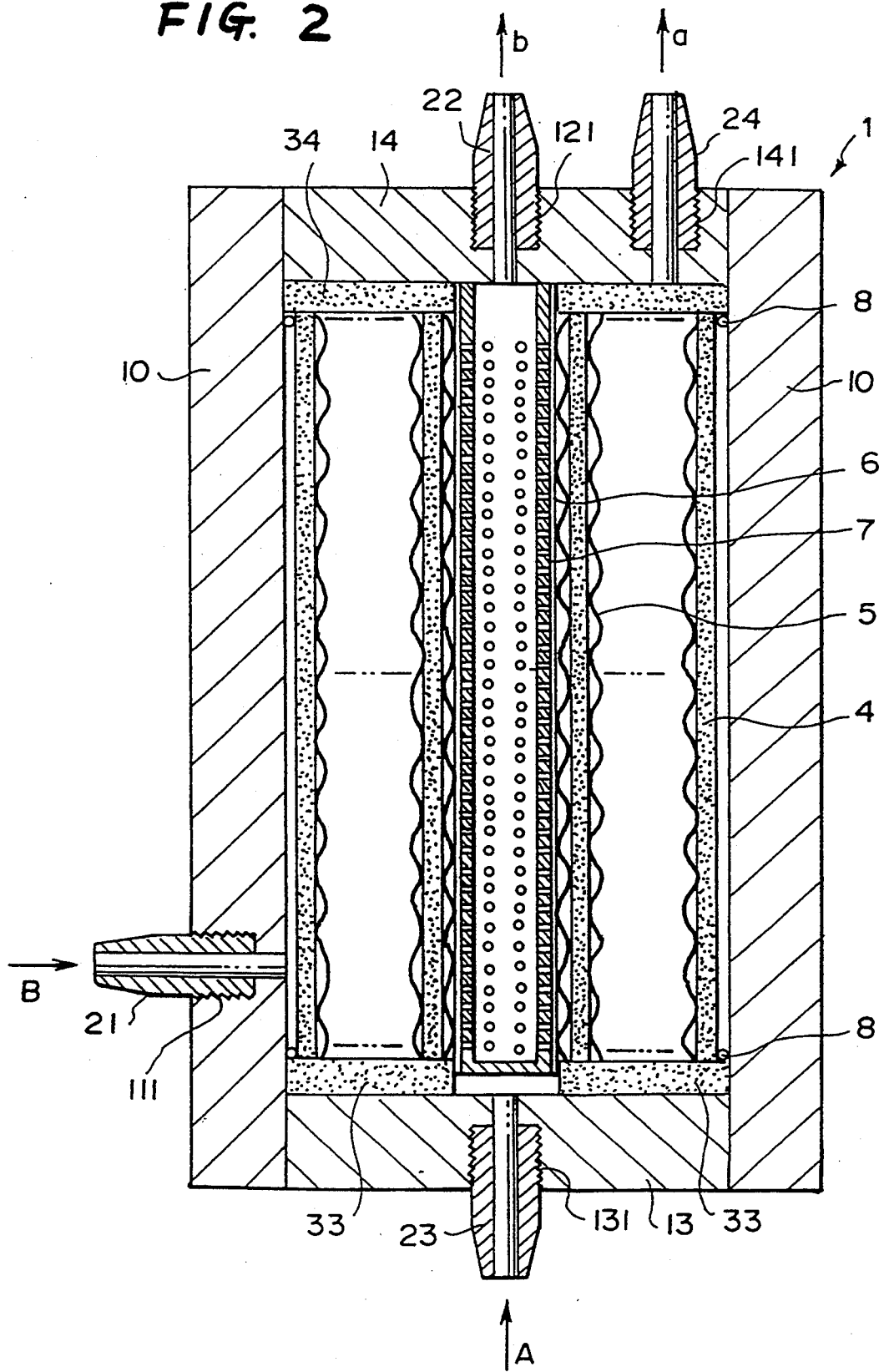
FIG. 2 is a sectional view of a bioreactor apparatus filled with spiral-type culture film as another embodiment of the present invention.

FIG. 2 is a sectional view showing the schematic configuration of a bioreactor using a spiral-shaped animal cell culture film, as another embodiment of the present invention. In the drawing, the container 1, which is different from that in the embodiment shown in FIG. 1, is composed of a tubular wall member 10, a lower wall member 13, and an upper wall member 14. This embodiment is similar to the previous embodiment (FIG. 1) in that two channel series (the supply channel A (23), the exhaust channel a (24), the supply channel B (21) and the exhaust channel b (22)) are provided in the container 1. In the embodiment shown in FIG. 2, the exhaust channel b (22), which is provided in the side wall member in the previous embodiment, is provided in the upper wall member. A hollow tube 7 having a large number of pores at the sides thereof is arranged at the center of the inside of the container. The upper end of the hollow tube 7 is connected to the center portion of the upper wall member 14 at a place containing the exhaust channel b in the inside thereof. That is, the hollow tube 7 is suspended from the upper wall member 14. A microfiltration membrane 6 is wound on the outer circumference of the hollow tube 7 so that the hollow tube 7 is coated with the microfiltration membrane 6. A culture film 4 and a sheet-like separator 5 are alternately wound on the outer circumference of the microfiltration membrane 6. The elements are packed in the container 1 and fixed in the inside of the container 1 by setting O-rings 8 to the upper and lower ends thereof on the outer circumference thereof. The gap between the side tubular wall 10 formed by the O-rings 8 and the wound matter is a space having the same function as that of the cavities 112 and 122 in the wall member in the previous embodiment. A rough porous plate 33 is arranged on the lower wall member 13 in the same manner as in the previous embodiment. A rough porous plate 34 is also arranged to the inner surface of the upper wall member 14. The opposite ends of the wound matter are fixed closely and tightly in the container 1 by the two porous plates.

A sterilizing treatment is applied to the apparatus of the invention by passing high-temperature vapor from the supply channel A to the exhaust channel b and from the supply channel B to the exhaust channel a for about 30 minute. Then, an aqueous solution containing about 1 g/l of specific animal cells is supplied from the supply channel A to the container 1 to produce a predetermined metabolite. The cell-containing solution enters into the container 1, reaches the rough porous plate 34 so as to be diffused to the whole surface thereof, propagates between the separators 5 in the container 1 to fill the container 1 and at the same time penetrates the pore tissue of the culture films 4. The animal cells in the aqueous solution contact onto the tissue surface of the culture films and then become adhered thereto. With the supply of the cell-containing solution, the amount of the adhered cells is increased. The time required for the adhesion of the sufficient amount of the animal cells is from about 30 to about 60 minutes.

After the deposition of the sufficient amount of the animal cells is confirmed, the supply of the animal cell-containing solution from the supply channel A is terminated and the supply of the culture solution from the supply channel B is started. The flow rate of the supplied culture solution is about 10 liters per day.

With the supply of the culture solution to the container 1, the animal cell-containing solution in the container 1 is gradually replaced by the culture solution. The entire replacement is finished about 30 minutes after the starting of the supply. Then, the supply of the culture is continued for about 24 hours, so that the animal cells in the container 1 are uniformly grown. As a result, animal cells can be cultivated to a high yield and a high density in the bioreactor apparatus of the invention. Then, a predetermined substrate is supplied for a period of one day to 3 days to produce a predetermined yield of the metabolite.

According to the bioreactor apparatus of the invention, animal cells with a high yield and a high density are deposited on the culture base arranged in the inside of the container and cultivated by liquid circulation culture technique. Accordingly, the supply and exchange of the culture solution can be performed automatically with ease. Further, an efficient metabolic reaction of animal cells can be performed by continuously controlling factors such as osmotic pressure, dissolved catalyst, pH, temperature, substrate concentration and metabolite concentration to optimum ranges suitable for cultivating the cells. Further, because the animal cells, the culture solution, the substrate and other necessary elements can be supplied in parallel to the culture bed carrier or perpendicularly thereto, these elements can be brought into efficient contact with the animal cells. Because the animal cells are deposited or fixed to the carrier so that there is no contact between the animal cells and between parts of the carrier, shear stress imposed on the cells is so small that inactivation of the cells infrequently occurs. Further, because the produced metabolite is continuously took out of the apparatus through the microfiltration membrane, there is no interference of the animal cells with the metabolite. As a result, a metabolic reaction of the animal cells progresses efficiently in the container.

What is claimed is:

1. A bioreactor apparatus, comprising:
    a hermetically sealed container having a first inlet disposed on a first wall for supplying a culture broth containing suspended animal cells to seed animal cells into the inside of said container;
    a second inlet for supplying and circulating a culture solution or a substrate solution into the inside of said container;
    a first outlet disposed on a second wall opposite said first wall for exhausting gas and an excess part of the culture broth from the inside of said container;
    a second outlet for exhausting and circulating a residual part of the culture solution or the substrate solution and a solution containing metabolites of the animal cells from the inside of said container;
    a first porous support plate disposed on an inner surface of said first wall so as to cover said first inlet;
    a second porous support plate disposed on an inner surface of said second wall so as to cover said first outlet;
    an animal cell culture base comprising at least one porous sheet carrier having sides coated with a culture bed layer suitable for adhesion of the animal cells, said at least one porous sheet carrier being positioned within the container such that a plurality of flow channels are formed between said sides, said channels being formed by spacers positioned between said sides and said channels extending between said first porous support plate and said second porous support plate such that said culture broth supplied from said first inlet flows through said first porous support plate to each of said channels and flows out of said channels through said second porous support plate to said first outlet; and
    a microfiltration membrane positioned within said container so as to cover said second outlet, said membrane for retaining suspended animal cells inside said container while allowing the passage of metabolites produced by the animal cells, said second inlet and said second outlet being positioned such that said culture solution or substrate solution penetrates the sides of said at least one sheet carrier while flowing from said second inlet through said membrane and out of said second outlet.

2. The apparatus of claim 1, wherein said at least one porous sheet carrier is made of nonwoven fabric.

3. The apparatus of claim 1, wherein said at least one porous sheet carrier is planar.

4. The apparatus of claim 1, wherein said culture base comprises a plurality of said porous sheet carriers wherein each of said sheet carriers is spaced from the other by said spacers so as to form said plurality of flow channels.

5. A bioreactor apparatus, comprising:
    a hermetically sealed tubular container including a tubular wall, a first sealed end and a second sealed end;
    a first inlet disposed on said first sealed end for supplying a culture broth containing suspended animal cells to seed animal cells into the inside of said container;
    a second inlet for supplying and circulating a culture solution or a substrate solution into the inside of said container;
    a first outlet disposed on said second sealed end for exhausting gas and an excess part of the culture broth from the inside of said container;
    a second outlet for exhausting and circulating a residual part of the culture solution or the substrate solution and a solution containing metabolites of the animal cells from the inside of said container;
    a first porous support plate disposed on an inner surface of said first sealed end so as to cover said first inlet;
    a second porous support plate disposed on an inner surface of said second sealed end so as to cover said first inlet;
    a hollow tube extending axially in said container so as to define an annular space therebetween, said tube having pores on the outer circumference thereof and said second outlet being in flow communication with the inside of said tube;
    an animal cell culture base comprising at least one porous sheet carrier having sides coated with a culture bed layer suitable for adhesion of the animal cells, said at least one porous sheet carrier being spirally wound within said annular space such that a plurality of flow channels are formed between said sides, said channels being formed by spacers positioned between said sides and said channels extending between said first porous support plate and said second porous support plate such that said culture broth supplied from said first inlet flows through said first porous support plate to each of said channels and flows out of said channels through said second porous support plate to said first outlet; and
    a microfiltration membrane circumscribing said tube in the inside of said container, said membrane for retaining suspended animal cells inside said container while allowing the passage of metabolites produced by the animal cells, said second inlet being positioned such that said culture solution or substrate solution supplied by said second inlet penetrates the sides of said at least one sheet carrier while radially flowing from said second inlet through said membrane and out of said second outlet.

6. The apparatus of claim 5, wherein said second inlet is disposed on said tubular wall.

7. The apparatus of claim 6, wherein said second outlet is disposed on the same end as said first outlet.

* * * * *